United States Patent [19]

Sorochenko

[11] Patent Number: 4,657,017
[45] Date of Patent: Apr. 14, 1987

[54] ELECTROSURGICAL INSTRUMENT

[75] Inventor: Oleg A. Sorochenko, Kharkov, U.S.S.R.

[73] Assignee: Nauchno-Isledovatelsky Institute Obshei I Neotlozhnoi Khirugii, Kharkov, U.S.S.R.

[21] Appl. No.: 769,622

[22] PCT Filed: Dec. 1, 1983

[86] PCT No.: PCT/SU83/00043
 § 371 Date: Jul. 30, 1985
 § 102(e) Date: Jul. 30, 1985

[87] PCT Pub. No.: WO85/02336
 PCT Pub. Date: Jun. 6, 1985

[51] Int. Cl.[4] .............................. A61B 17/36
[52] U.S. Cl. .................... 128/303.14; 128/303.17; 30/263; 30/276
[58] Field of Search ................ 128/303.13, 303.14, 128/303.15, 303.16, 303.17, 305, 310, 312; 30/240, 263, 265, 276

[56]  References Cited

U.S. PATENT DOCUMENTS 1,179,434  2/1913  Hunt .......................... 30/240
3,651,811  3/1972  Hildebrandt et al. ........... 128/303.17
4,202,156  5/1980  Golyanovsky et al. ........... 30/276

FOREIGN PATENT DOCUMENTS 21089    of 1908  Australia .................. 30/276
2060397  5/1981   United Kingdom .
194982   6/1967   U.S.S.R. .
639561   2/1979   U.S.S.R. .

OTHER PUBLICATIONS

An advertisement for "High Frequency Electrosurgical Instrument" (undated).
S. Ja. Doletsky et al., High-Frequency Electrosurgery, 1980, Meditsina, Publ., Moscow, pp. 48-55.

Primary Examiner—Kyle L. Howell
Assistant Examiner—Randy Citrin
Attorney, Agent, or Firm—Fleit, Jacobson, Cohn & Price

[57] ABSTRACT

An electrosurgical instrument comprises a cutting working portion (1) which incorporates two ring-shaped electrodes (3, 4) separated with a disk (2) from an insulating material, a power actuator to impart rotation to the working portion (1), and current leads, each adapted to interact with the respective ring electrode (3 or 4). The cutting working portion (1) is additionally provided with a knife (14) whose cutting edge (15) is shaped as a circular arc whose size is not in excess of 90 arc degrees of the outer circumference of the working portion (1). The cutting edge (15) may stand over the outer circumference of the disk (2), or be an integral part thereof.

1 Claim, 7 Drawing Figures

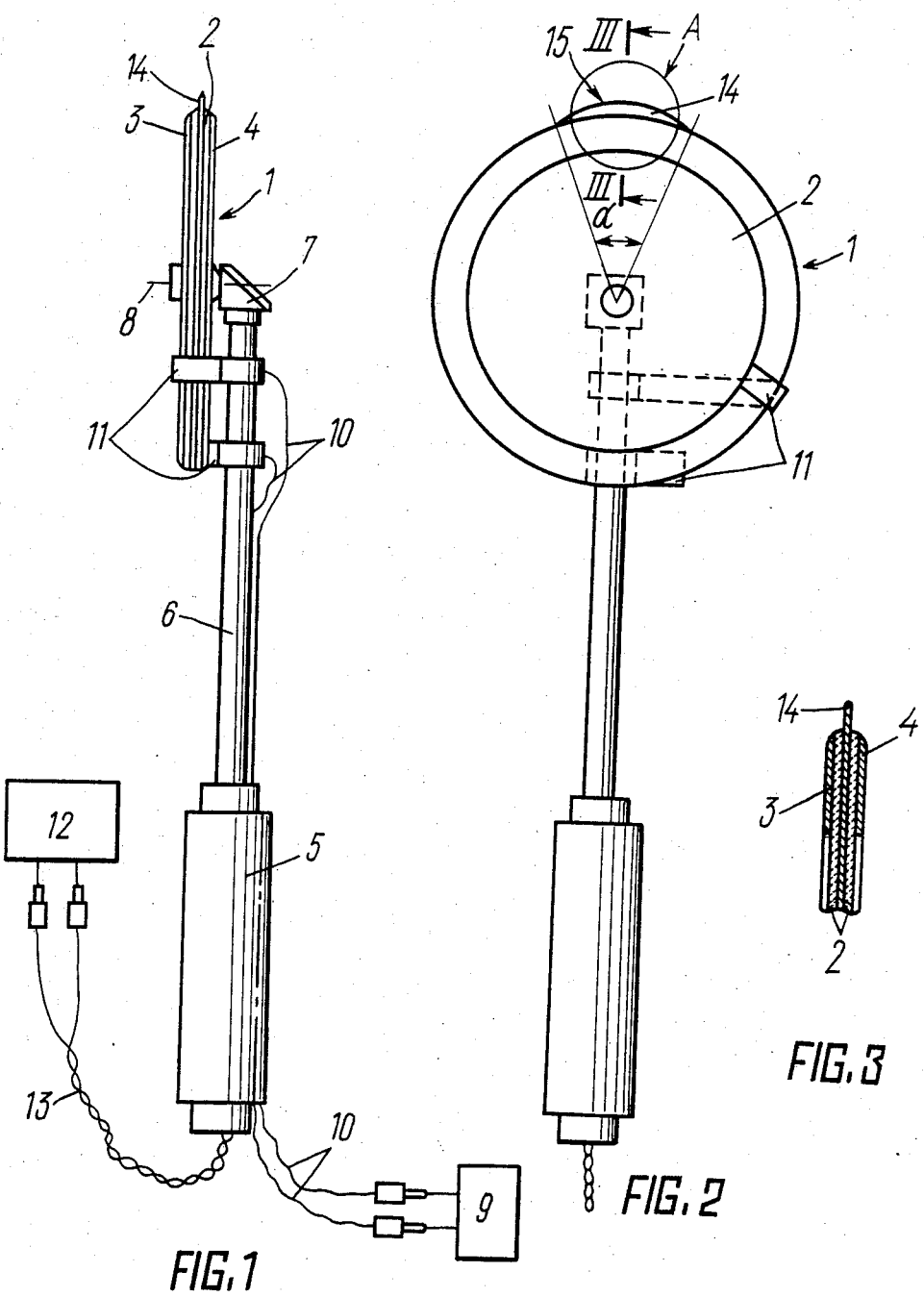

ELECTROSURGICAL INSTRUMENT

TECHNICAL FIELD

The present invention relates to surgery and more specifically to electrosurgical instruments for bloodless surgical procedures on various organs and tissues.

BACKGROUND ART

Known in the art an electrosurgical instrument which is in fact a knife either straight or bent at 30 degrees, serving as an active electrode connected to a source of diathermic current (cf. an advertisement prospectus for "The 3C-3O r.f. electrosurgical apparatus").

The aforementioned knife-like instruments are monoactive, i.e., requiring the other passive plate-electrode, applied to the body of the patient operated upon a certain distance apart from the knife.

Use of a passive electrode in surgical procedures leads to complications, viz., damaging the organs and tissues on the path of an r.f. current flowing from an active knife-electrode to a passive electrode, or burns of tissues situated under the passive electrode. Furthermore, it is due to r.f. current dispersion in the tissues lying between the knife and the passive electrode and useless heating of the tissues that operative procedures on internal organs become uncontrolled and proceed unstably. In addition, the instrument is to be additionally cleaned of the coagulate deposit.

Another electrosurgical instrument is known to comprise a cutting working portion shaped as two ring-electrodes separated with an insulant disk, a mechanical actuator to impart rotation to the working portion, and current leads, each interacting, through its electric contact, with the respective ring electrode. The electric contacts are made as springy knives interacting with the end faces of the electrodes (cf. USSR Inventor's Certificate No. 639,561 published 1978).

In the aforesaid instrument both of the ring electrodes are active, and the length of path of an r.f. current from electrode to the other is as short as fractions of a millimeter. Coagulate deposit is removed from the electrodes by knife-shaped current leads. Getting the active electrodes rid of coagulate deposit and shaping the cutting working portion as a rotary disk makes it possible to establish a stable r.f. current field within the operative wound, which adds much to the efficacy of the surgery performed.

However, the known biactive electrosurgical instrument enables mostly surgery on the parenchymatous organs, and its function boils down to bloodless cutting of the parenchyma without slitting open the lumen of major blood vessels, which is attained due to the instrument's cutting lips being shaped as an oval. Thus, the heretofore-known electrosurgical instrument produces a destructive effect upon the tissue due to the action of a diathermic current alone, without a mechanical cutting effect, which renders the instruments inapplicable for bloodless surgery on soft (muscular) tissues, as well as for dissection of the skin, fasciae and ligaments.

DISCLOSURE OF THE INVENTION

The present invention has for its principal object the provision of an electrosurgical instrument whose construction makes it possible to conduct bloodless surgery on the muscular tissue, as well as to dissect the skin and tissues containing fasciae and ligaments.

The aforesaid object is accomplished due to the fact that in an electrosurgical instrument, comprising a cutting working portion which incorporates two ring-shaped electrodes isolated with an insulating disk, a power actuator to impart rotation to the working portion, and current leads, each adapted to interact with the respective ring-shaped electrode, according to the invention, the cutting working portion is additionally provided with a knife whose cutting edge is shaped as a circular arc the size of which is not in excess of 90 arc degrees of the outer circumference of the working portion.

The knife may be built into the insulating disk in such a manner that its cutting edge projects beyond the outer circumference of the insulating disk.

The knife may also be made from the material of the insulating disk and integral therewith.

The knife may likewise be made of the material of the electrodes integral therewith so that the electrode cutting edge should protrude beyond the working portion outer circumference.

It is expedient that one of the electrodes and the insulating disk have a segmental cut, and that the segmental portion of the other electrode protruding beyong the segmental cut should perform the function of a knife.

The electrosurgical instrument made in accordance with the present invention, is a bipolar biactive one, which enables, due to combination of a mechanical and a diathermocoagulation cutting edge, performing bloodless surgery on the muscular tissue, dissecting the skin and tissues containing fasciae and ligaments, with practically no injury to patient's tissues and organs lying out of the operative wound.

In what follows the present invention will now be disclosed in a detailed description of some specific illustrative embodiments thereof with reference to the accompanying drawings, wherein:

FIG. 1 is a general schematic view of an electrosurgical instrument;

FIG. 2 is a side view of the electrosurgical instrument of FIG. 1;

FIG. 3 is a scaled-up sectional view of an area A in FIG. 1 taken on the line III—III;

Figure 4:
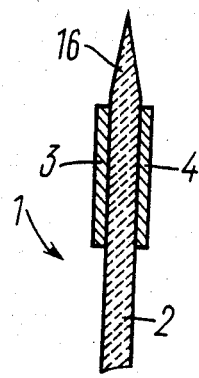
FIG. 4 is a view of FIG. 3 showing the knife made integral with the insulating disk.

The electrosurgical instrument of the present invention (FIGS. 1 and 2) comprises a working cutting portion or assembly 1 shaped as a disk 2 of an insulating material, carrying ring-shaped metallic electrodes 3, 4. Rotation to the working portion 1 is imparted by a power actuator which incorporates an electric motor 5 linked, through an output shaft 6 and a gear speed reducer 7, to pivot pin 8 about which the working portion 1 rotates. The electrodes 3, 4 are electrically connected to a source 9 of a diathermic current through current leads 10 and movable contacts 11 which are made as springy knives, each of them contacting the end face of the respective electrode 2 or 3. The electric motor 5 is connected to a power source 12 through a cord 13.

Built into the disk 2 is a mechanical knife 14 arranged in symmetry with the ring electrodes 3, 4. A cutting edge 15 of the mechanical knife 14 stands above the outer circumference of the disk 2 and is not in excess of the 90 arc degrees of the entire cutting edge of the working portion 1 (represented as an angle α in the drawings). In this particular embodiment the angle α is adopted to be 50 degrees.

In an embodiment of the working portion 1 of the electrodurgical instrument as represented in FIG. 4, a knife 16 is made of same material as the insulating disk 2 and integral therewith, and the cutting edge 15 of the knife 16 protrudes beyond the outer circumference or periphery of the working portion 1.

Figure 5:
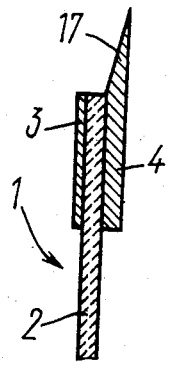
FIG. 5 is a view of FIG. 3 showing the knife made integral with the electrode.

In an embodiment of the working portion 1 as illustrated in FIG. 5, a knife 17 is made of the same material as the electrode 4 and integral therewith, and the cutting edge of the knife 17 protrudes beyond the outer circumference of the working portion 1.

Figure 6:
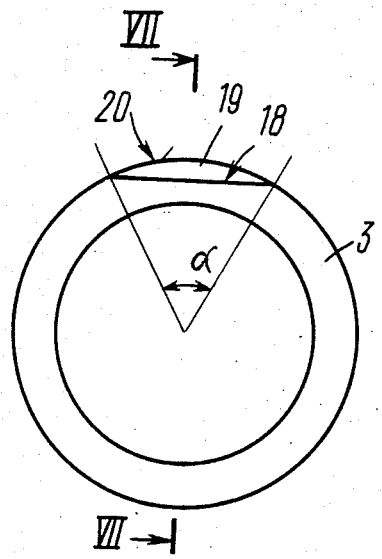
FIG. 6 shows an embodiment of the cutting portion of the electrosurgical instrument disclosed herein, showing one of the electrodes and the insulating disk having a segmental cut.
Figure 7:
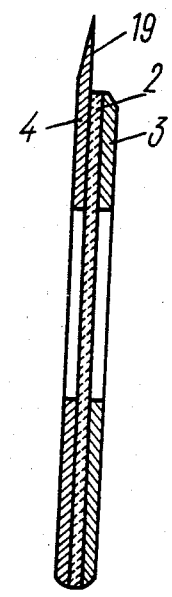
FIG. 7 is a scaled-up sectional view taken on the line VII—VII in FIG. 6.

In an embodiment of the working portion as presented in FIGS. 6 and 7, the electrode 3 and the insulating disk 2 have identical segmental outer portions removed along chordal cuts 18 and the segment of the electrode 4 adjacent the cuts 18 serves as a knife 19. A cutting edge 20 of the knife 19 in this case is in fact an extension to the outer circumference of the working portion 1.

The application techniques of electrosurgical instrument of the invention are as follows.

First the electric motor 5 is switched on, rotation being transmitted therefrom to the working portion 1 through the output shaft 6 and the gear speed reducer 7. Simultaneously an r.f. current is applied to the ring electrodes 3, 4 through the current leads 10 and the movable contacts 11, with the result that an r.f. electric field is established across said electrodes 3, 4. Once the rotary working portion 1 has been brought in contact with the living tissue, the mechanical knife 14 (16, 17, 19) having the sharp cutting edge 15 (20), dissects the tissue, while the remainder of the surface of the working portion 1 produces electrocoagulation of the blood and lymphatic vessels that have previously been dissected by the mechanical knife 14 (16, 17, 19). Thus, cyclic cutting processes are continually repeated in the course of surgery, each of them incorporating the step of mechanically dissecting the tissue with the cutting edge 15 (20) of the mechanical knife 14 (16, 17, 19), and the step of electro-coagulation of the dissected tissue with an oval-shaped edge of the disk 2 carrying the ring electrodes 3, 4. The coagulated tissue stuck to the working portion 1 is continuously removed with the movable contacts 11 made as pringy blades, when the disk 2 is rotating.

Experiments have demonstrated that an efficacious bloodless dissection of living tissues is practicable with a ratio of the cutting time to the electrocoagulation time ranging within 1:35 and 1:3, that is, the cutting edge 15 (20) of the mechanical knife 14 (16, 17, 19) should equal 10 to 90 arc degrees of the working portion 1. With the cutting edge 15 (20) of a smaller size some difficulties arise in dissecting the living tissue, while with that edge of a larger size, electrocoagulation process proves to be of low efficacy so that no bloodless surgery could be attained.

The instrument having the cutting edge 15 of the mechanical knife 14 (16, 17) protruding beyond the outer circumference or periphery of the disk 2 (FIGS. 1, 2, 3, 4, 5) is reasonable to be applied for surgery on tissues containing ligaments, pronounced elastic fibres and cartilages, since an increased cutting effect should be produced.

The instrument having the cutting edge 20 (FIGS. 6, 7) of the mechanical knife 19 is flush with the outer circumference of the disk 2 is for surgery on the muscular and mucoid tissues, e.g., in gastrectomy or colectomy, and in surgical treatment of wounds.

The cutting edge 15 (20) of the mechanical knife 14 (16, 17, 19) may be of any shape inherent in diverse surgical instruments. Good results have been obtained in experiments with a cutting edge shaped as the blade of a surgical scalpel. To good advantage has been used (for treatment of infected wounds) a wavy cutting edge resembling the blade of a domestic knife intended for slicing freshly baked bread.

INDUSTRIAL APPLICABILITY

The electrosurgical instrument, according to the invention, is for performing bloodless surgery in medicine and veterinary medicine, and is preferably applicable for surgery on soft tissues, such as muscles and fasciae.

I claim:

1. An electrosurgical instrument, comprising a disk-shaped cutting assembly which has an outer periphery and which includes two ring-shaped electrodes isolated by a disk of an insulating material, a power actuator drivingly connected to the disk-shaped assembly to impart rotation to the disk-shaped assembly, and current leads electrically connected to respective ones of the ring-shaped electrodes, one of the electrodes and the insulating disk each having a segmental outer portion removed essentially along a chordal cut and a segmental outer portion of the other electrode standing over the segmental cut defining a knife having a cutting edge which extends along a circular arc the size of which is not in excess of 90 arc degrees of the outer periphery of the disk-shaped cutting assembly, so that the knife and an electrical field established across the ring-shaped electrodes cause cyclic mechanical cutting of tissue and electrocoagulation of cut tissue, respectively, as the disk-shaped cutting assembly is rotated by the power actuator.

* * * * *